United States Patent
Ushida et al.

(10) Patent No.: US 10,792,474 B2
(45) Date of Patent: Oct. 6, 2020

(54) GUIDEWIRE

(71) Applicant: ASAHI INTECC CO., LTD., Seto-shi, Aichi (JP)

(72) Inventors: Keisuke Ushida, Nagoya (JP); Toshiyuki Yoshida, Seto (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 735 days.

(21) Appl. No.: 15/450,850

(22) Filed: Mar. 6, 2017

(65) Prior Publication Data

US 2018/0064913 A1 Mar. 8, 2018

Related U.S. Application Data

(63) Continuation of application No. PCT/JP2016/075978, filed on Sep. 5, 2016.

(51) Int. Cl.
*A61B 5/00* (2006.01)
*A61M 25/09* (2006.01)

(52) U.S. Cl.
CPC ... *A61M 25/09* (2013.01); *A61M 2025/09083* (2013.01); *A61M 2025/09133* (2013.01);
(Continued)

(58) Field of Classification Search
CPC .... A61M 25/005; A61M 25/00; A61M 25/09; A61M 25/0662; A61B 2017/00938;
(Continued)

(56) References Cited

U.S. PATENT DOCUMENTS 4,554,929 A * 11/1985 Samson .......... A61M 25/09033
600/434
4,922,924 A * 5/1990 Gambale ............... A61M 25/09
600/434

(Continued)

FOREIGN PATENT DOCUMENTS

EP 0 405 823 B2 1/1999
EP 0 770 404 B1 2/2002
(Continued)

OTHER PUBLICATIONS

Oct. 10, 2017 Notification of Reasons for Refusal issued in Japanese Patent Application No. 2016-571364.

*Primary Examiner* — May A Abouelela
(74) *Attorney, Agent, or Firm* — Oliff PLC (57) ABSTRACT

A guidewire includes a core shaft, a coil body disposed around an outer periphery of the core shaft, and a resin layer. The resin layer includes a proximal end part disposed around an outer periphery of the coil body; a distal end part located between the core shaft and the coil body distal to the proximal end part and having an outer diameter that is smaller than an outer diameter of the proximal end part; and a tapered part located between the proximal end part and the distal end part and having an outer diameter that decreases in the distal direction. The distal end part of the coil body is not covered with the resin layer. The guidewire has improved rotation performance (operativity) while maintaining insertability, and a risk that a distal end the resin layer will detach from the guidewire is reduced.

22 Claims, 12 Drawing Sheets

(52) U.S. Cl.
CPC ............ *A61M 2025/09175* (2013.01); *A61M 2025/09191* (2013.01)

(58) Field of Classification Search
CPC ........... A61B 2017/00942; A61B 2017/30052; A61B 5/6851
USPC ......... 600/300, 585; 604/526, 528; 140/71 C
See application file for complete search history.

(56) References Cited

U.S. PATENT DOCUMENTS

| | | | | |
|---|---|---|---|---|
| 5,107,852 A | * | 4/1992 | Davidson | A61L 29/085 600/585 |
| 5,129,890 A | | 7/1992 | Bates et al. | |
| 5,443,907 A | * | 8/1995 | Slaikeu | A61M 25/09 428/375 |
| 5,549,580 A | | 8/1996 | Diaz | |
| 5,830,155 A | | 11/1998 | Frechette et al. | |
| 5,840,046 A | * | 11/1998 | Deem | A61M 25/09 600/585 |
| 6,183,420 B1 | * | 2/2001 | Douk | A61M 25/09 600/434 |
| 7,753,859 B2 | | 7/2010 | Kinoshita et al. | |
| 8,167,821 B2 | * | 5/2012 | Sharrow | A61M 25/0108 600/433 |
| 8,403,867 B2 | * | 3/2013 | Nowak, Jr. | A61M 25/09 600/585 |
| 9,028,428 B2 | * | 5/2015 | Maki | A61M 25/09 600/585 |
| 2008/0004546 A1 | * | 1/2008 | Kato | A61M 25/09 600/585 |
| 2008/0154152 A1 | * | 6/2008 | Satou | A61M 25/09 600/585 |
| 2008/0234606 A1 | * | 9/2008 | Itou | A61M 25/09 600/585 |
| 2010/0004561 A1 | * | 1/2010 | Nabeshima | A61M 25/09 600/585 |
| 2011/0178504 A1 | * | 7/2011 | Maki | A61M 25/09 604/528 |
| 2011/0245730 A1 | * | 10/2011 | Satozaki | A61L 31/10 600/585 |
| 2011/0319872 A1 | * | 12/2011 | Kawasaki | A61M 25/09 604/528 |
| 2012/0059279 A1 | * | 3/2012 | Kawasaki | A61L 31/022 600/585 |
| 2012/0197159 A1 | * | 8/2012 | Miyata | A61M 25/09 600/585 |
| 2013/0131642 A1 | * | 5/2013 | Miyata | A61M 25/09 604/528 |
| 2015/0306347 A1 | * | 10/2015 | Yagi | A61M 25/0067 604/526 |
| 2015/0335857 A1 | * | 11/2015 | Ishikawa | A61M 25/005 604/526 |
| 2016/0074631 A1 | * | 3/2016 | Otani | B21F 3/02 600/585 |

FOREIGN PATENT DOCUMENTS

| | | |
|---|---|---|
| EP | 2 014 329 B1 | 10/2016 |
| JP | H03-051060 A | 3/1991 |
| JP | 2007-075531 A | 3/2007 |
| JP | 2008307367 A | 12/2008 |

\* cited by examiner

GUIDEWIRE

CROSS REFERENCE TO RELATED APPLICATION

This application is a continuation of PCT/JP2016/075978 filed on Sep. 5, 2016, the contents of which are incorporated by reference herein in their entirety.

BACKGROUND

The disclosed embodiments relate to a medical device. Specifically, the disclosed embodiments relate to a guidewire to be inserted into a blood vessel or a digestive organ.

When a blood vessel, bile duct, pancreatic duct, or the like (that is, a vessel) includes a narrowed or obstructed segment, flow of blood, bile (gall), or pancreatic fluid, respectively, is usually restricted. Therapeutic procedures using a catheter are widely performed as a measure for treating such a narrowed or obstructed segment.

A guidewire is commonly used in order to guide a catheter to a narrowed or obstructed segment of a vessel. If there is a high frictional resistance between the guidewire and the vessel wall, it may be difficult for an operator to insert the guidewire into a narrowed or obstructed segment of the vessel. A known guidewire includes a coil body and a resin layer covering an entire length of an outer periphery of the coil body to facilitate insertion of the guidewire into a narrowed or obstructed segment (see Japanese Patent Application Laid-Open No. 2007-075531 and Japanese Patent Application Laid-Open No. 2008-307367).

In the guidewire according to Japanese Patent Application Laid-Open No. 2007-075531, an outer periphery of a coil body is covered with a resin film (resin layer) throughout its entire length. Similarly, in the guidewire according to Japanese Patent Application Laid-Open No. 2008-307367, an outer periphery of a coil body is covered with a resin coating layer throughout its entire length.

The resin layers provided on the coil bodies of these guidewires can reduce frictional resistance, and thus allow easier insertion of the guidewires into narrowed or obstructed segments. However, the guidewires have the following disadvantages: the rotation performance of the guidewire is poor (the operativity of the guidewire is poor); and the stiffness of a distal end part of the guidewire tends to be high.

SUMMARY

The disclosed embodiments have been devised in view of these circumstances. An object of the disclosed embodiments is to provide a guidewire having improved rotation performance (improved operativity) while maintaining the insertability of the guide, and having a reduced risk that a distal end of a resin layer will detach (peel off) from the guidewire.

The above object can be achieved by virtue of the structure discussed below.

A guidewire of the disclosed embodiments includes a core shaft; a coil body wound around (disposed around) an outer periphery of the core shaft; and a resin layer including a proximal end part having a large outer diameter, a distal end part positioned distal to the proximal end part and having an outer diameter smaller than that of the proximal end part, and a tapered part positioned between the distal end part and the proximal end part and having an outer diameter that decreases toward its distal end. The proximal end part covers an outer periphery of the coil body, and the distal end part is located between the core shaft and the coil body so that the coil body is exposed (i.e., is not covered with the resin layer). The resin layer having this configuration can improve the rotation performance of the guidewire (the operativity of the guidewire) while maintaining the insertability of the guidewire, and can reduce the risk that a distal end of the resin layer will detach (peel off) from the guidewire.

The distal end part of the resin layer may be fixed to the core shaft, reducing a risk that a distal end of the resin layer will project outward from the guidewire, as well as reducing a risk that the distal end of the resin layer will detach (peel off) from the guidewire.

The guidewire may include a bulged portion provided at the distal end part of the resin layer. The bulged portion has an outer diameter larger than that of the distal end part. If the distal end of the resin layer begins to detach from the guidewire, the bulged portion will get caught at an inner periphery surface of the coil body, providing an anchoring effect. This further reduces the risk that the resin layer will detach form the guidewire.

The guidewire may include a fixation portion that fixes the core shaft, the coil body, and the resin layer together at a boundary of the tapered part of the resin layer and the proximal end part of the resin layer. When a guidewire is inserted into a narrowed or obstructed segment of a vessel, frictional resistance with the vessel wall becomes high at the boundary of the tapered part of the resin layer and the proximal end part of the resin layer. However, the risk that the resin layer will detach from the guidewire at the boundary of the tapered part and the proximal end part upon insertion of the guidewire is reduced because the resin layer is fixed to the coil body and the core shaft through the fixation portion.

The coil body may include multiple wires. That is, the coil body may be formed by spirally winding multiple wires. In this case, the distal end part of the resin layer enters into a space between adjacent wires of the multiple wires of the coil body as viewed in cross section, creating an anchoring effect between the distal end part of the resin layer and the coil body. The resin layer can therefore be further prevented from detaching from the guidewire.

The coil body may include a small-diameter portion (proximal) located at a position corresponding to the proximal end part of the resin layer; a large-diameter (distal) portion having a coil outer diameter larger than that of the small-diameter portion and being located at a position corresponding to the distal end part of the resin layer; and an increasing-diameter portion having a coil outer diameter increasing toward its distal end and being located at a position corresponding to the tapered part of the resin layer. The coil outer diameter at the large-diameter portion of the coil body is larger than the outer diameter of the proximal end part of the resin layer. This reduces a risk that the vessel wall will contact the boundary of the tapered part of the resin layer and the proximal end part of the resin layer even when the guidewire is inserted into a curved vessel. As a result, the resin layer at the boundary of the tapered part and proximal end part is further prevented from detaching from the guidewire upon insertion of the guidewire into the vessel.

DETAILED DESCRIPTION OF EMBODIMENTS

Figure 1:
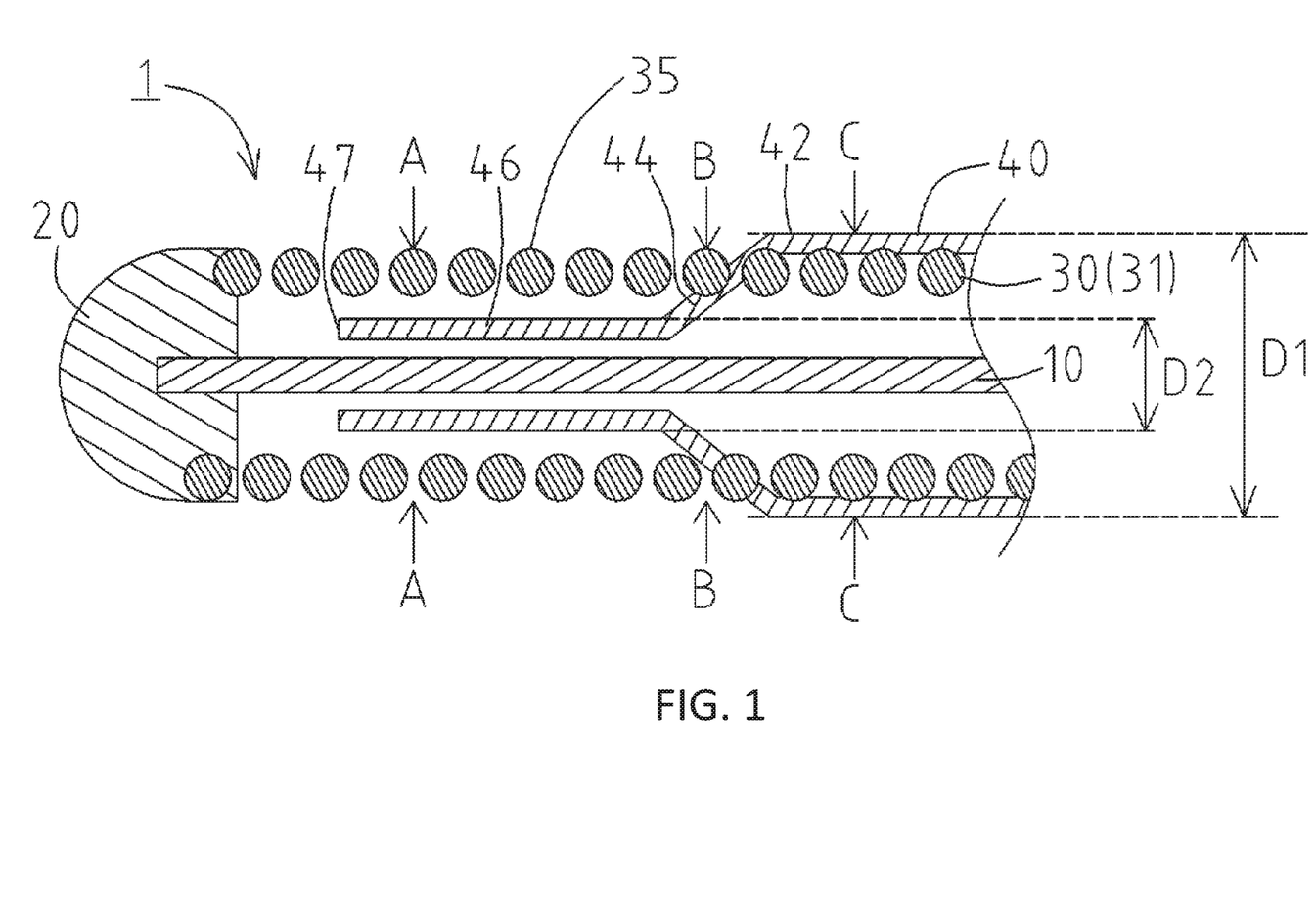
FIG. 1 shows a guidewire according to the disclosed embodiments.
Figure 2:
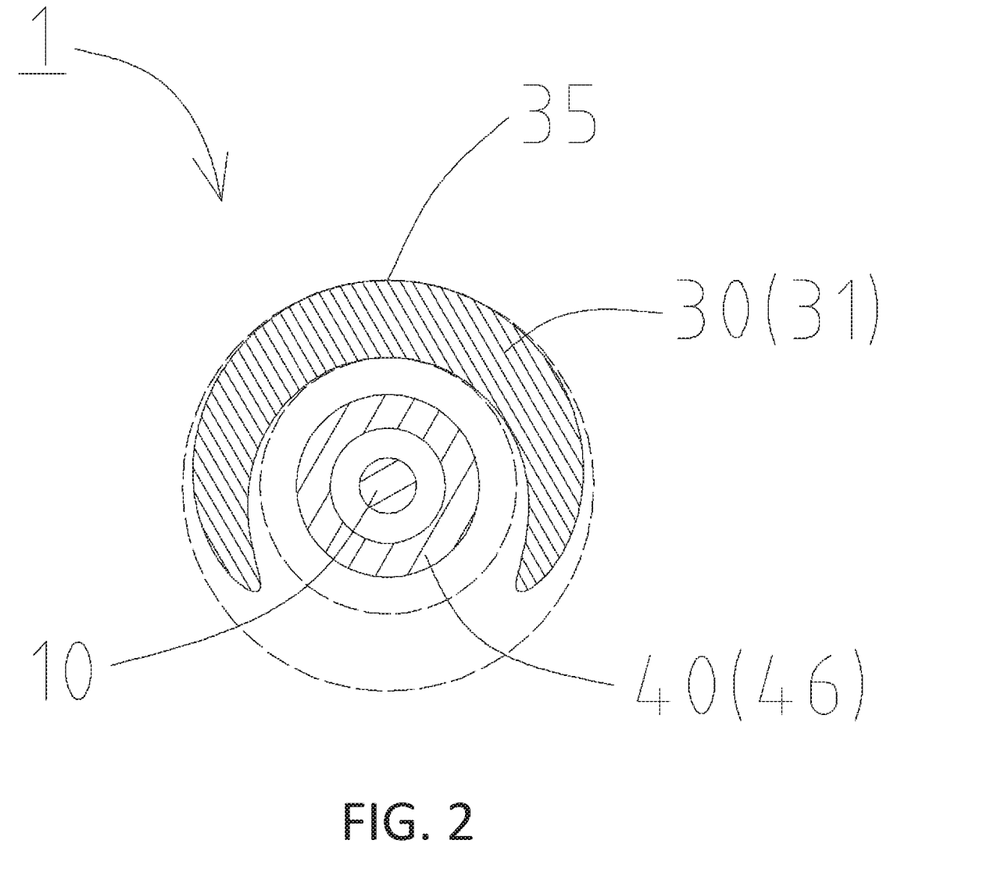
FIG. 2 shows a cross sectional view taken along line A-A shown in FIG. 1.
Figure 3:
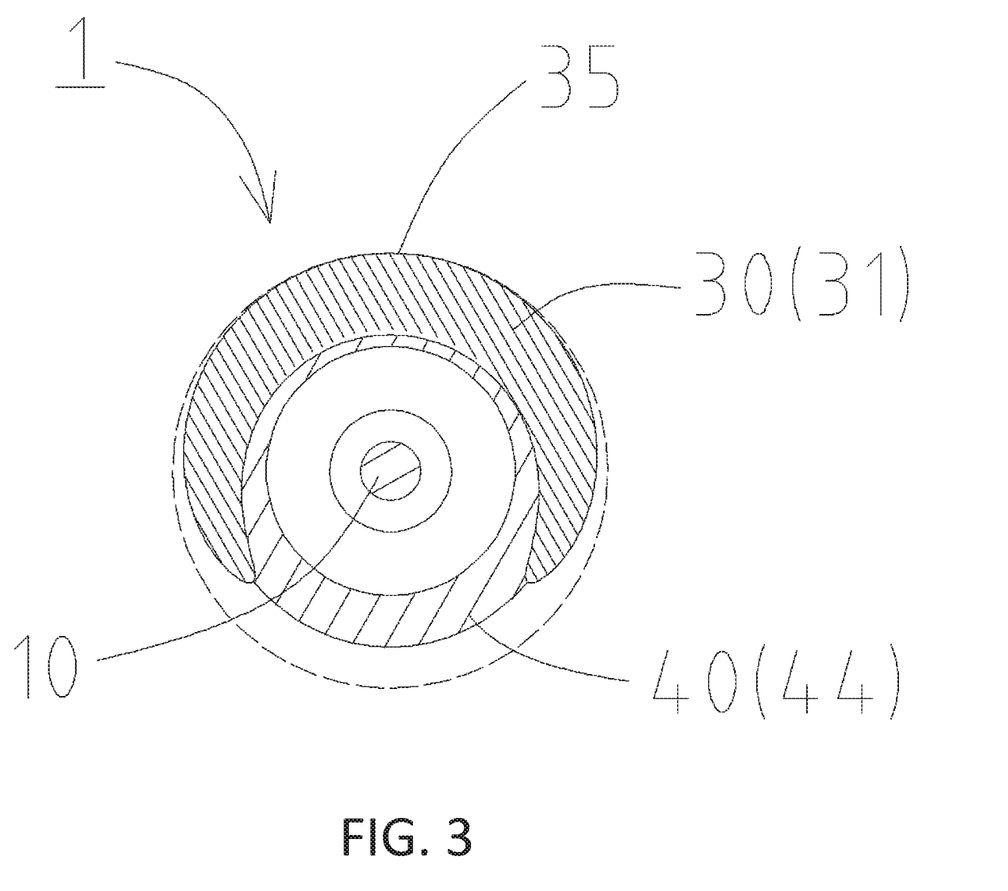
FIG. 3 shows a cross sectional view taken along line B-B shown in FIG. 1.
Figure 4:
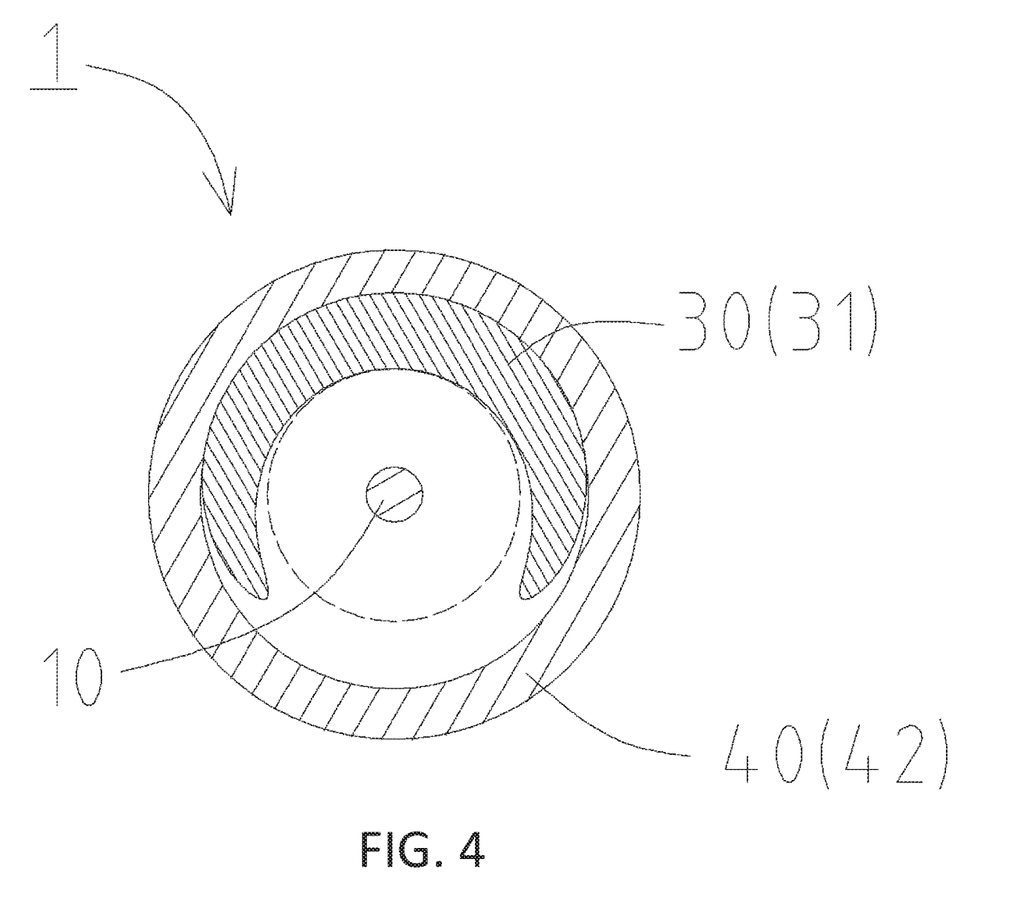
FIG. 4 shows a cross sectional view taken along line C-C shown in FIG. 1.

A guidewire 1 according to the disclosed embodiments will be described with reference to FIGS. 1 to 4. In FIG. 1 (as well as in later-described FIGS. 5-9 and 12) the left side corresponds to a distal end (a front end), which is to be inserted into the body, and the right side corresponds to a proximal end (a base end), which is to be operated by an operator such as a physician. FIG. 2 shows a cross section of the guidewire 1 taken along line A-A shown in FIG. 1, FIG. 3 shows a cross section of the guidewire 1 taken along line B-B shown in FIG. 1, and FIG. 4 shows a cross section of the guidewire 1 taken along line C-C shown in FIG. 1.

The guidewire 1 may be used, for example, to guide a catheter to a narrowed or obstructed segment of a vessel. As shown in FIG. 1, the guidewire 1 includes a core shaft 10, a distal end fixed part 20, a coil body 30, and a resin layer 40.

The core shaft 10 may be made of stainless steel (SUS 304, SUS 316, or the like), a superelastic alloy of a Ni—Ti alloy, or the like.

The coil body 30 is formed by winding a single wire 31 around an outer periphery of the core shaft 10. The single wire 31 may be radiopaque. Materials which can be used for the wire 31 of the coil body 30 include, for example, gold, platinum, tungsten, and alloys of these elements. In a case where the coil body 30 is formed with the wire 31 having radiopacity, an operator can detect the position of the coil body 30 using radiography imaging.

The distal end fixed part 20 fixes a distal end of the core shaft 10 to a distal end of the coil body 30, and is formed with a solder material (an aluminum alloy solder, a silver solder, a gold solder, an Au—Sn alloy, an Ag—Sn alloy, or the like).

The resin layer 40 includes a proximal end part 42 having an outer diameter D1 and covering the outer periphery of the coil body 30; a distal end part 46 having an outer diameter D2 smaller than the outer diameter D1 of the proximal end part 42 and being located between the core shaft 10 and the coil body 30 distal to the proximal end part 42; and a tapered part 44 having an outer diameter decreasing from D1 to D2 in the distal direction between the proximal end part 42 and the distal end part 46.

Materials which can be used for the resin layer 40 as described above include polyurethane, polyethylene, polyvinyl chloride, polyester, polypropylene, polyamide, a fluorinated resin such as polytetrafluoroethylene (PTFE), a silicone resin, and the like.

As shown in FIGS. 1 and 2, the distal end part 46 of the resin layer 40 is located between the core shaft 10 and the coil body 30. As shown in FIGS. 1 and 3, a distal end of the tapered part 44 of the resin layer 40 is located inside the coil body 30, and a proximal end of the tapered part 44 of the resin layer 40 is located at the outer periphery of the coil body 30. As shown in FIGS. 1 and 4, the proximal end part 42 of the resin layer 40 is located at the outer periphery of the coil body 30.

An outer periphery surface 35 of the coil body 30 is exposed (i.e., is not covered with the resin layer 40) at its distal end, but is covered with the tapered part 44 and the proximal end part 42 of the resin layer 40 at its proximal end (see FIG. 1). Accordingly, the distal end of the coil body 30 is not covered by the distal end part 46 of the resin layer 40.

Because the coil body 30 is exposed at its distal end, the rotation performance of the guidewire 1 (the operativity of the guidewire 1) is improved, and yet the insertability of the guidewire 1 is maintained by virtue of the proximal end part 42 of the resin layer 40. Furthermore, a distal end 47 of the resin layer 40 is prevented from detaching from the guidewire 1 when the guidewire 1 is inserted into a vessel because the distal end part 46 of the resin layer 40 is located inside the coil body 30.

Figure 5:
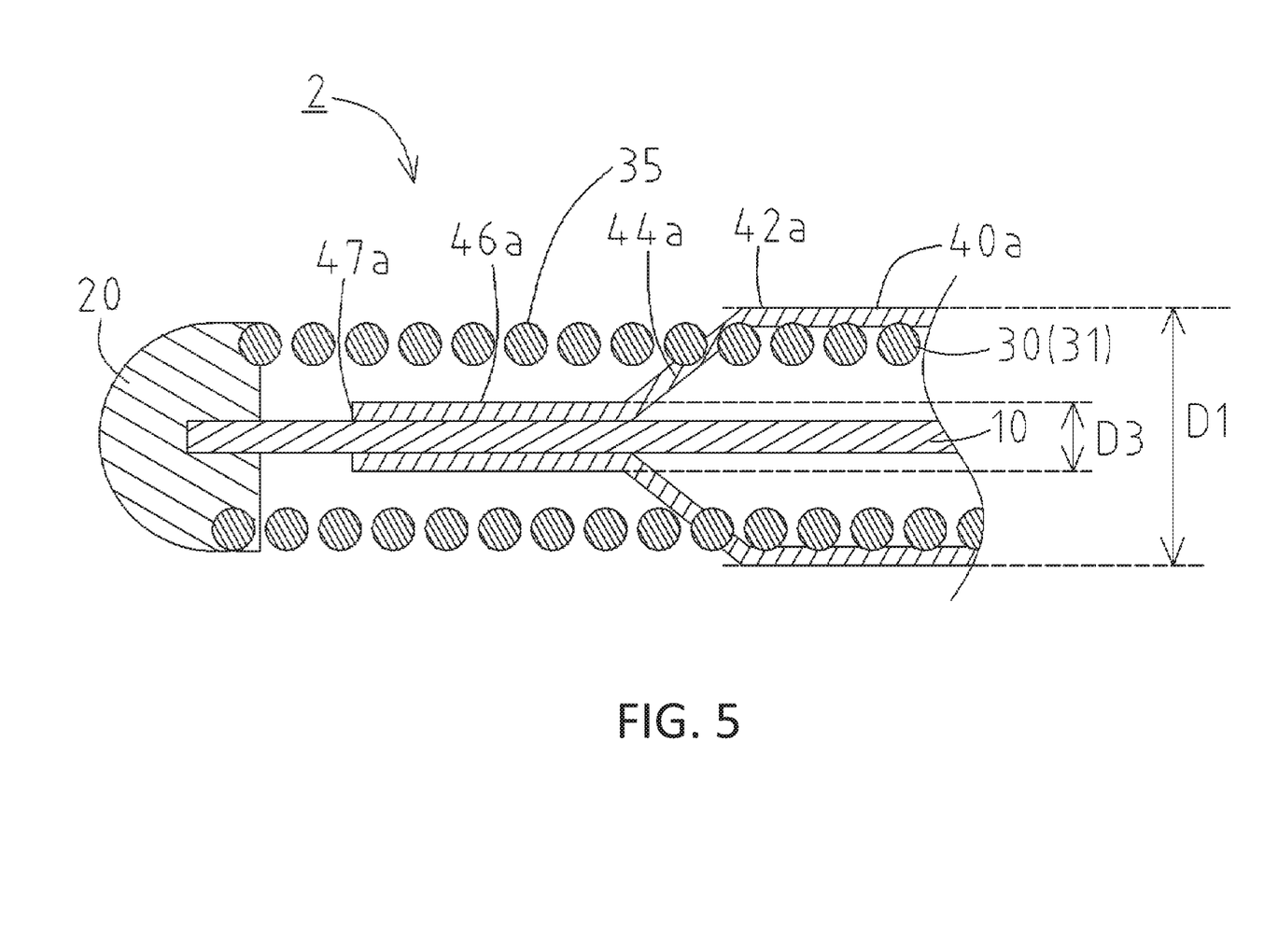
FIG. 5 shows a guidewire according to the disclosed embodiments.

Next, a guidewire 2 according to the disclosed embodiments will be described with reference to FIG. 5. Only differences from the guidewire 1 as shown in FIG. 1 will be described.

In the guidewire 2, a resin layer 40a includes a proximal end part 42a having the large outer diameter D1 and covering the outer periphery of the coil body 30; a distal end part 46a having an outer diameter D3 smaller than that of the proximal end part 42a and being located between the core shaft 10 and the coil body 30 distal to the proximal end part 42a; and a tapered part 44a having an outer diameter decreasing from D1 to D3 in the distal direction between the proximal end part 42a and the distal end part 46a. Further, the distal end part 46a of the resin layer 40a is fixed to the core shaft 10.

This configuration can reduce a risk that a distal end 47a of the resin layer 40a will project outward from between the wires 31 of the coil body 30, and can reduce a risk that the distal end 47a the resin layer 40a will detach from the guidewire 2 even when the guidewire 2 is inserted into a curved vessel.

Next, a guidewire 3 according to the disclosed embodiments will be described with reference to FIG. 6. Only differences from the guidewire 2 as shown in FIG. 5 will be described. In the guidewire 3, a resin layer 40b includes the proximal end part 42a, the tapered part 44a, and the distal end part 46a, and a bulged portion 50 is provided at the distal end 47a of the distal end part 46a and has an outer diameter D4 larger than the outer diameter D3 of the distal end part 46a. Further, the distal end part 46a of the resin layer 40b and the bulged portion 50 are fixed to the core shaft 10.

In the guidewire 3, the bulged portion 50 is integrally formed of the same material as the resin layer 40b, but the configuration is not limited to this. The bulged portion 50 may be formed of a material which is different from that of the distal end part 46a of the resin layer 40b.

The bulged portion 50 is provided at the distal end 47a of the distal end part 46a of the resin layer 40b. If the resin layer 40b begins to detach from the distal end of the guidewire 3, the bulged portion 50 will get caught at an inner periphery surface 36 of the coil body 30, providing an anchoring effect. This further reduces the risk that the resin layer 40b will detach from the guidewire 3.

Figure 6:
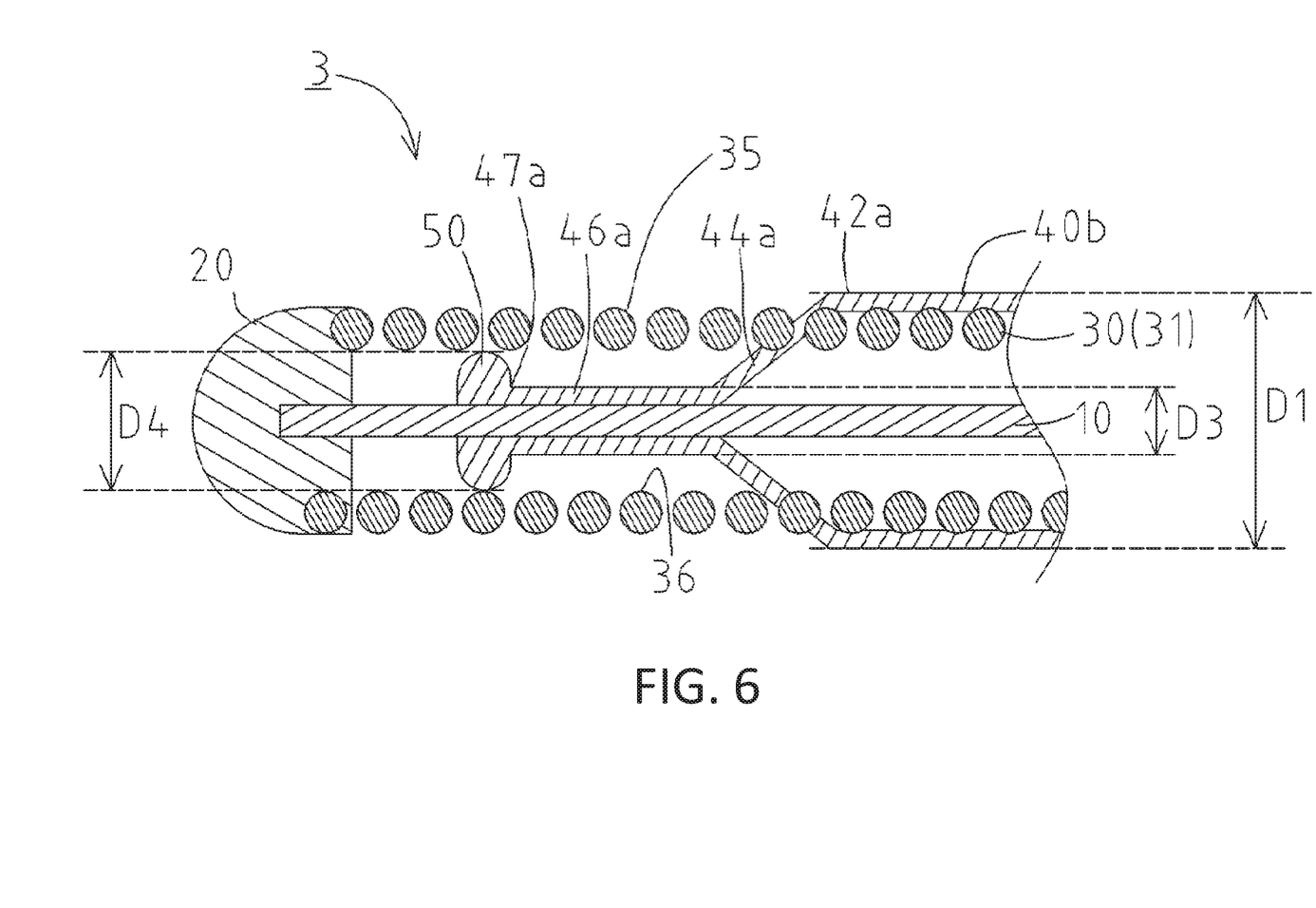
FIG. 6 shows a guidewire according to the disclosed embodiments.

Note that in the guidewire 3 as shown in FIG. 6, the distal end part 46a of the resin layer 40b and the bulged portion 50 are fixed to the core shaft 10. The configuration, however, is not limited to this. In the guidewire 4 shown in FIG. 7, only a bulged portion 50a, and not the distal end part 46 of a resin layer 40c, is fixed to the core shaft 10. The resin layer 40c includes the proximal end part 42, the tapered part 44, and the distal end part 46. The bulged portion 50a has the outer diameter D4 larger than the outer diameter D2 of the distal end part 46 and is provided at the distal end 47 of the distal end part 46.

Figure 7:
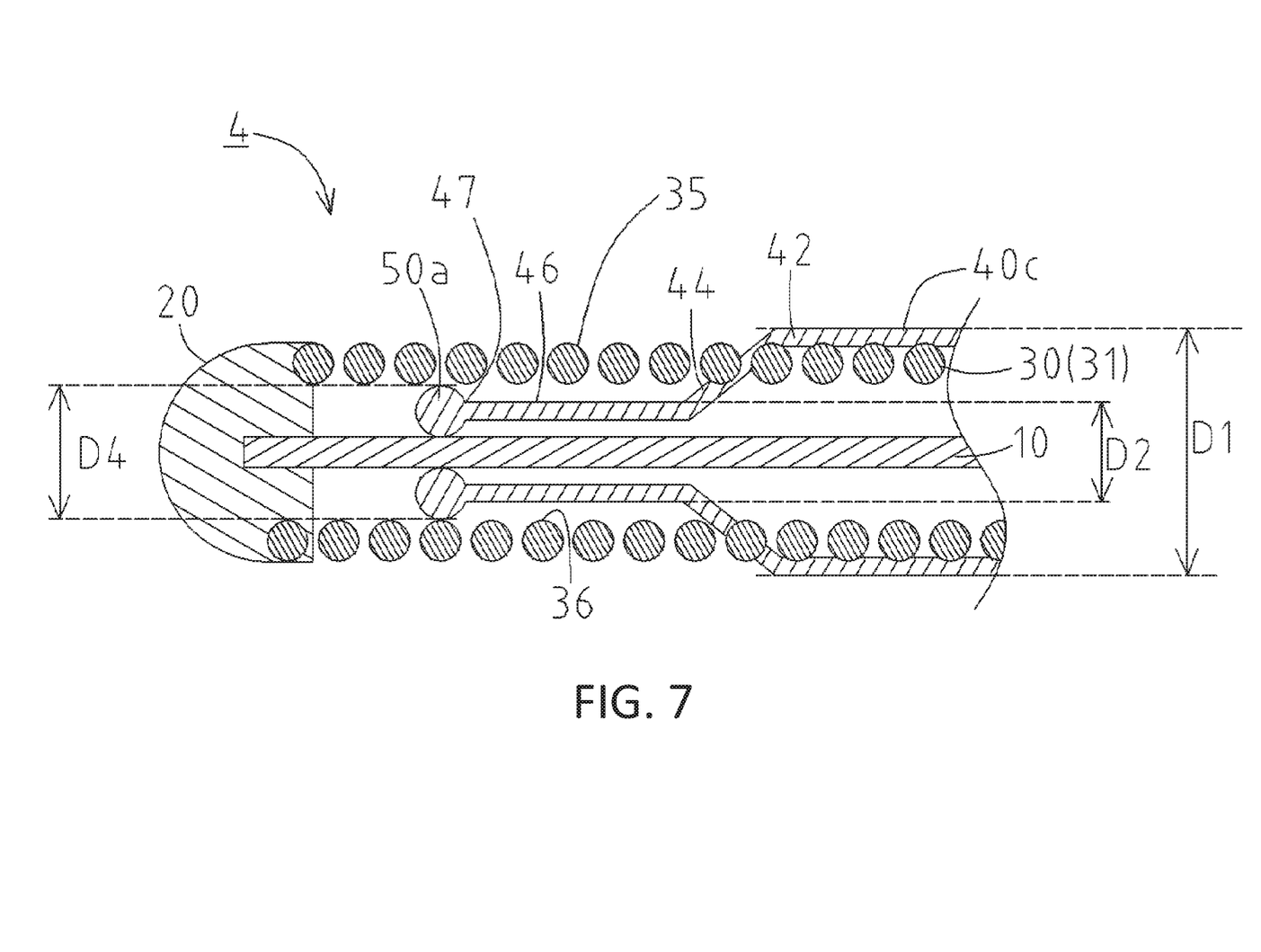
FIG. 7 shows a guidewire according to the disclosed embodiments.

In the guidewire 4, the bulged portion 50a is integrally formed of the same material as the resin layer 40c, but the configuration is not limited to this. The bulged portion 50a may be formed of a material which is different from that of the distal end part 46 of the resin layer 40c.

The bulged portion 50a is provided at the distal end 47 of the distal end part 46 of the resin layer 40c. If the resin layer 40c begins to detach from the distal end of the guidewire 4, the bulged portion 50a will get caught at the inner periphery surface 36 of the coil body 30, providing an anchoring effect. This further reduces the risk that the resin layer 40c will detach from the guidewire 4.

Figure 8:
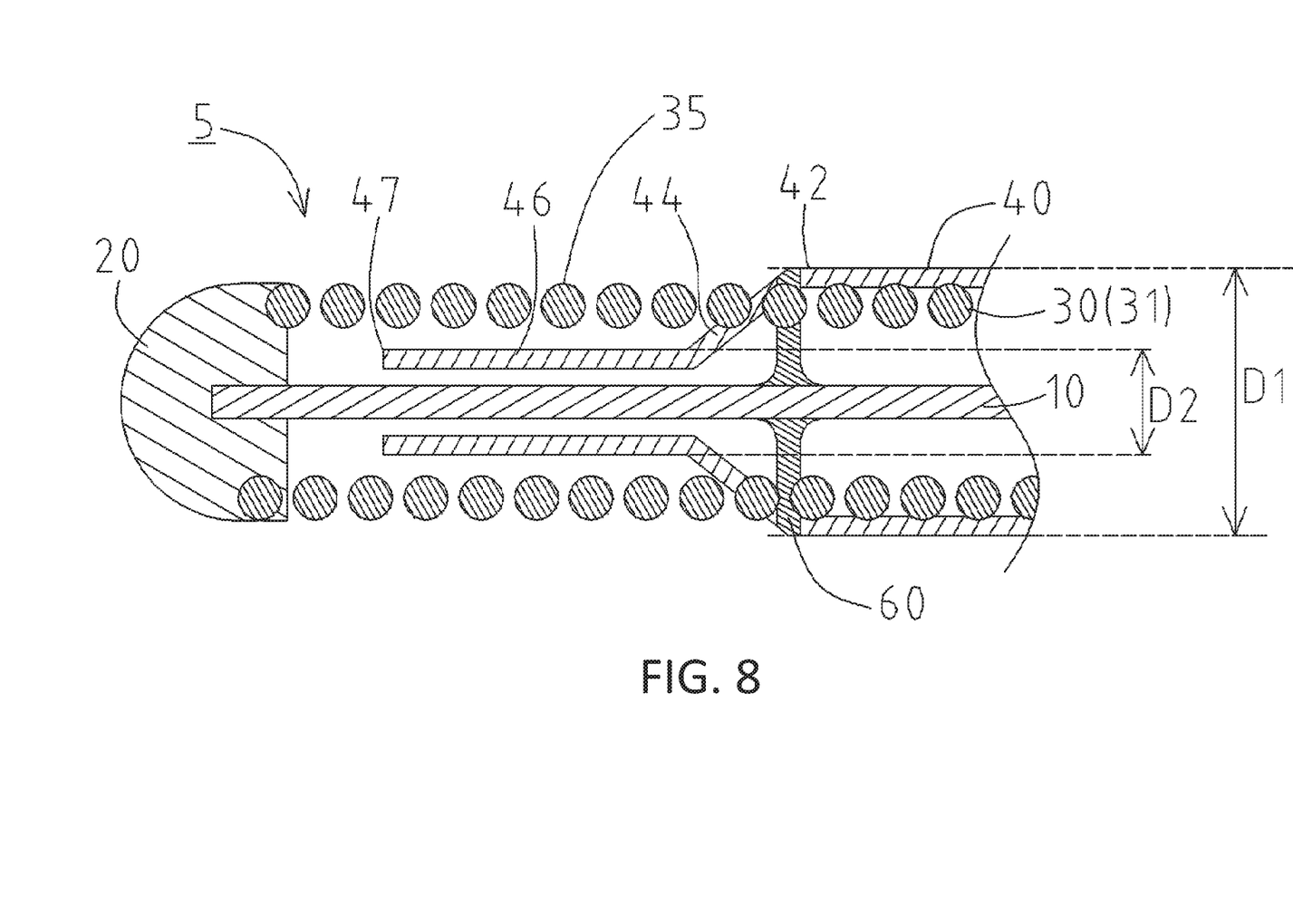
FIG. 8 shows a guidewire according to the disclosed embodiments.

Next, a guidewire 5 according to the disclosed embodiments will be described with reference to FIG. 8. In the guidewire 5, a fixation portion 60 fixing the resin layer 40 to the core shaft 10 and the coil body 30 is provided at a boundary of the tapered part 44 of the resin layer 40 and the proximal end part 42 of the resin layer 40.

In the guidewire 5, the resin layer 40 is fixed to the coil body 30 and the core shaft 10 through the fixation portion 60. This further reduces the risk that the resin layer 40 will detach from the guidewire 5 at the boundary of the tapered part 44 and the proximal end part 42 of the resin layer 40 upon insertion of the guidewire 5 into the vessel, even when the guidewire 5 is inserted into a narrowed or obstructed segment of the vessel (and thus the frictional resistance between the guidewire 5 and the vessel wall is high at the boundary of the tapered part 44 of the resin layer 40 and the proximal end part 42 of the resin layer 40).

Note that an adhesive is used as the fixation portion 60 in the guidewire 5, but there is no particular limitation for the material thereof.

Next, a guidewire 6 according to the disclosed embodiments will be described with reference to FIG. 9. Only differences from the guidewire 1 as shown in FIG. 1 will be described. In the guidewire 6, a coil body 30a is formed by spirally winding ten wires 31a (see FIG. 10). Further, as shown in FIG. 9, a resin layer 40d includes a proximal end part 42b having the outer diameter D1 and covering an outer periphery of the coil body 30a; a distal end part 46b having an outer diameter D5 smaller than the outer diameter D1 of the proximal end part 42b and being located between the core shaft 10 and the coil body 30a distal to the proximal end part 42b; and a tapered part 44b having an outer diameter decreasing from D1 to D5 in the distal direction between the proximal end part 42b and the distal end part 46b.

Figure 9:
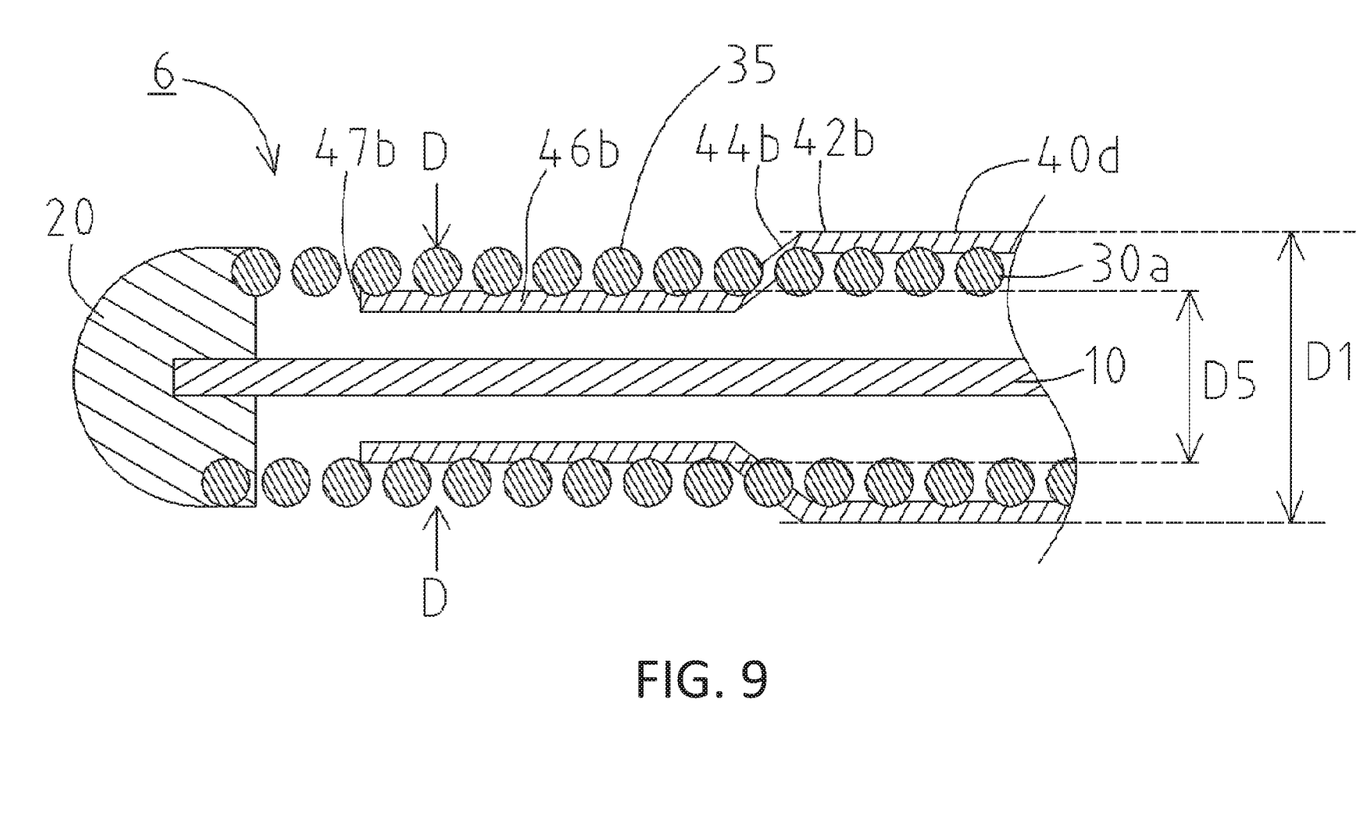
FIG. 9 shows a guidewire according to the disclosed embodiments.
Figure 10:
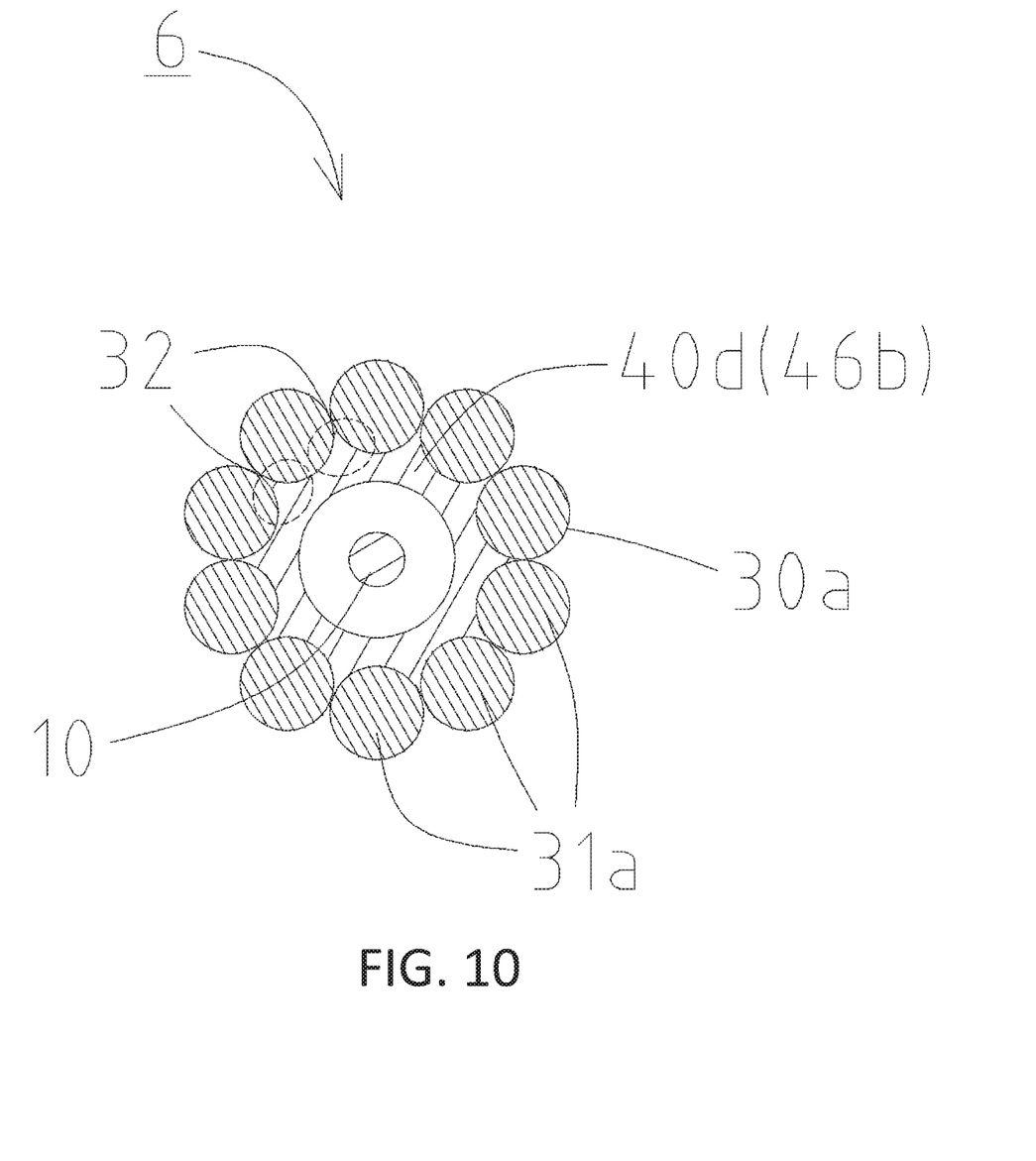
FIG. 10 shows a cross sectional view taken along line D-D shown in FIG. 9.

As shown in FIG. 10, which shows a cross section of the guidewire 6 taken along the line D-D shown in FIG. 9, the distal end part 46b of the resin layer 40d enters into a space 32 between adjacent wires of the multiple wires 31a of the coil body 30a, creating an anchoring effect. This further reduces the risk that the distal end part 46b of the resin layer 40 will detach from the guidewire 6 because the distal end part 46b of the resin layer 40d can become caught at the space 32 between adjacent wires of the multiple wires 31a.

Figure 11:
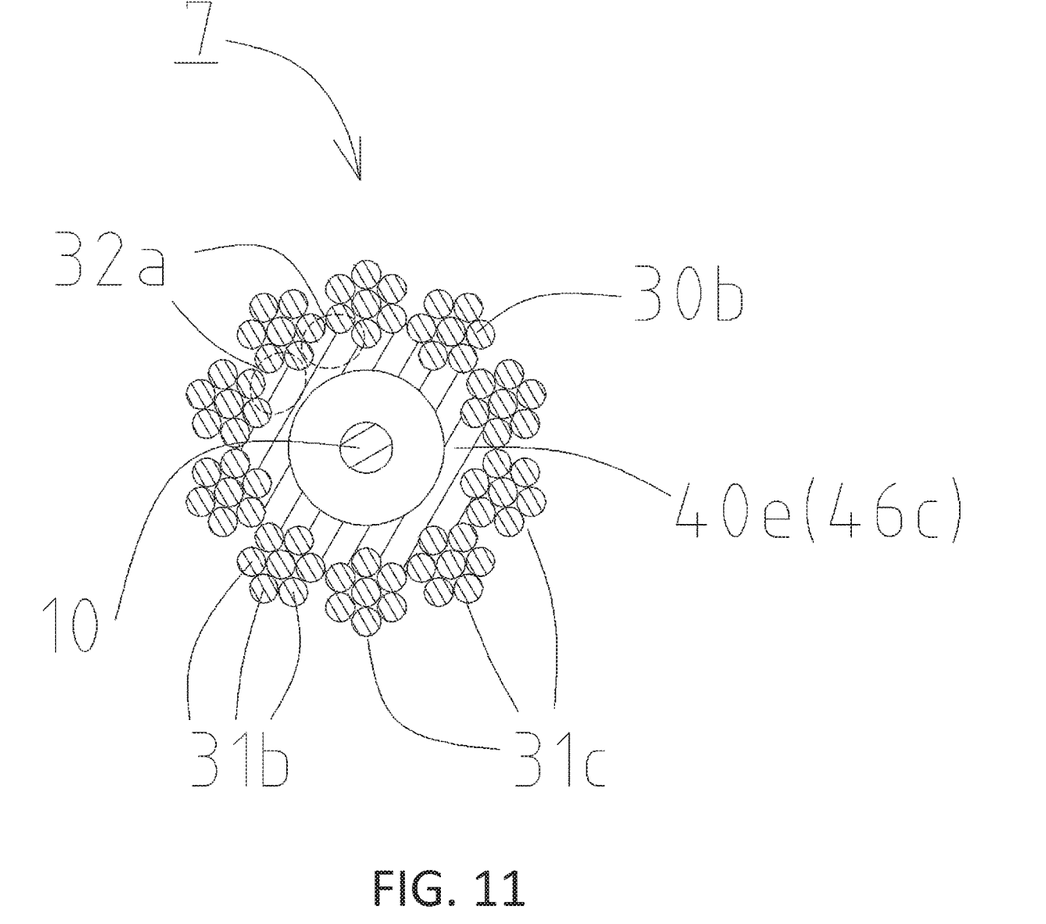
FIG. 11 shows a cross sectional view of a guidewire according to the disclosed embodiments.

Note that in the guidewire 6 as shown in FIG. 10, the coil body 30a is formed by spirally winding ten wires 31a. However, the configuration is not limited to this. In a guidewire 7 shown in FIG. 11, a coil body 30b is formed by bundling and spirally winding ten twisted wires 31c, each twisted wire 31c including seven wires 31b spirally wound together. Here, as shown in FIG. 11, a distal end part 46c of a resin layer 40e enters into a space 32a between adjacent twisted wires 31c of the coil body 30b, creating an anchoring effect.

This further reduces the risk that the distal end part 46c of the resin layer 40e will detach from the guidewire 7 because the distal end part 46c of the resin layer 40e can become caught at the space 32a between adjacent twisted wires 31c.

Materials which can be used for the multiple wires 31a of the coil body 30a or the multiple wires 31b of the coil body 30b include, for example, gold, platinum, tungsten, and alloys of these elements as in the wires 31 of the guidewire 1. Note that the number of the multiple wires 31a of the coil body 30a is not limited to ten. Any number of wires 31a may be used as long as there are more than one. Further, the number of the twisted wires 31c of the coil body 30b is not limited to ten, either. Any number of twisted wires 31c may be used as long as there are more than one. Furthermore, the number of the multiple wires 31b of the twisted wires 31c as described above is not limited to seven, either. Any number of wires 31b may be used as long as there are more than one.

Figure 12:
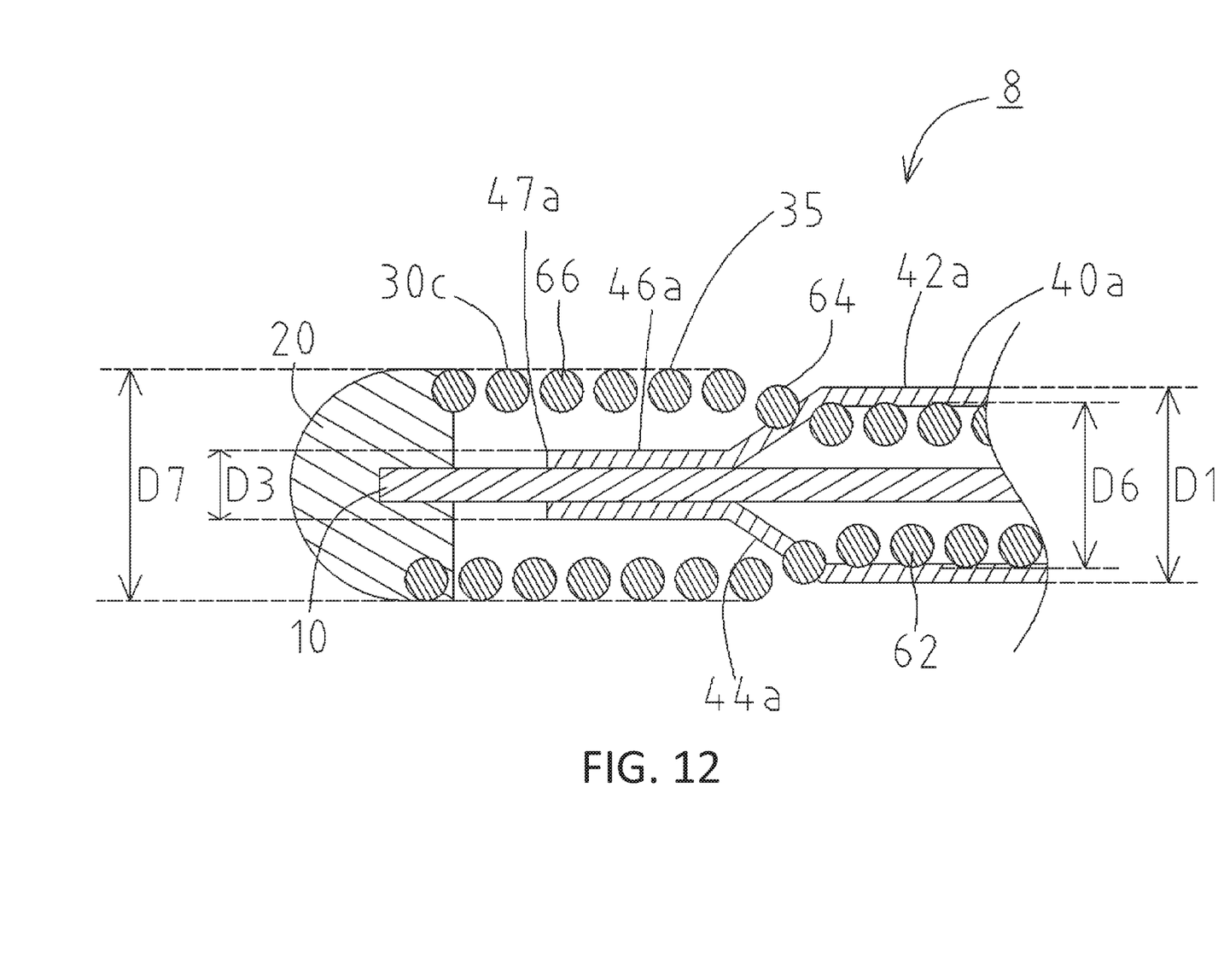
FIG. 12 shows a guidewire according to the disclosed embodiments.

Next, a guidewire 8 according to the disclosed embodiments will be described with reference to FIG. 12. Only differences from the guidewire 2 as shown in FIG. 5 will be described. In the guidewire 8, a coil body 30c includes a small-diameter portion 62 having a coil outer diameter D6 and being located at a position corresponding to the proximal end part 42a of the resin layer 40a; a large-diameter portion 66 having a coil outer diameter D7 larger than the coil outer diameter D6 of the small-diameter portion 62 and being located at a position corresponding to the distal end part 46a of the resin layer 40a; and an increasing-diameter portion 64 having a coil outer diameter increasing from D6 to D7 in the distal direction and being located at a position corresponding to the tapered part 44a of the resin layer 40a. In other words, a distal end of the small-diameter portion 62 is at a same position along a longitudinal axis of the guidewire 8 as a distal end of the proximal end part 42a of the resin layer 40a; and a proximal end of the large-diameter portion 66 is at a same position along the longitudinal axis as a proximal end of the distal end part 46a of the resin layer 40a. Further, the coil outer diameter D7 of the large-diameter portion 66 of the coil body 30c is larger than the outer diameter D1 of the proximal end part 42a of the resin layer 40a (D7>D1).

This reduces the risk that the boundary of the tapered part 44a of the resin layer 40a and the proximal end part 42a of the resin layer 40a will contact the vessel wall even when the guidewire 8 is inserted into a curved vessel. As a result, the resin layer 40a can be further prevented from detaching from the guidewire 8 upon insertion of the guidewire 8 into the vessel.

Note that in guidewires 5, 6, 7, 8, the bulged portions 50, 50a may be provided at the distal ends 47, 47a, 47b of the distal end parts 46, 46a, 46b, 46c as in the guidewires 3, 4.

Further, in the guidewires 2, 3, 4, 6, 7, 8, the fixation portion 60 fixing the core shaft 10, the coil bodies 30, 30a, 30b, 30c, and the resin layers 40a to 40e may be provided at the boundary of the tapered parts 44, 44a, 44b and the proximal end parts 42, 42a, 42b as in the guidewire 5.

Furthermore, in the guidewires 1, 3, 4, 5, 6, 7, the coil bodies 30, 30a, 30b may include the small-diameter portion 62 having the coil outer diameter D6 and being located at a position corresponding to the proximal end parts 42, 42a, 42b of the resin layers 40 and 40b to 40e; the large-diameter portion 66 having the coil outer diameter D7 larger than the coil outer diameter D6 of the small-diameter portion 62 and being located at a position corresponding to the distal end parts 46 to 46c of the resin layers 40 and 40b to 40e; and the increasing-diameter portion 64 having a coil outer diameter increasing from D6 to D7 in the distal direction and being located at a position corresponding to the tapered parts 44, 44a, 44b of the resin layers 40 and 40b to 40e. The coil outer diameter D7 of the large-diameter portion 66 of the coil bodies 30, 30a, 30b may be larger than the outer diameter D1 of the proximal end parts 42, 42a, 42b of the resin layers 40 and 40b to 40e (D7>D1) as in the guidewire 8.

Note that in the guidewires 1 to 8 as described above, the distal ends 47, 47a, 47b of the distal end parts 46 to 46c of the resin layers 40 to 40e are spaced from the distal end fixed part 20 in the proximal direction (that is, the distal ends 47, 47a, 47b are separated from the distal end fixed part 20), but the configuration is not limited to this. For example, the distal ends 47, 47a, 47b of the distal end parts 46 to 46c of the resin layers 40 to 40e and the distal end fixed part 20 may be fixed to each other.

What is claimed is:

1. A guidewire comprising: a core shaft;
a coil body disposed around an outer periphery of the core shaft; and
a resin layer including:
a proximal end part disposed around an outer periphery of the coil body,
a distal end part located between the core shaft and the coil body distal to the proximal end part, the distal end part having an outer diameter that is smaller than an outer diameter of the proximal end part, and
a tapered part located between the proximal end part and the distal end part and having an outer diameter that decreases in a distal direction,
wherein a distal end of the coil body is not covered with the resin layer.

2. The guidewire according to claim 1, wherein the distal end part of the resin layer is fixed to the core shaft.

3. The guidewire according to claim 1, further comprising:
a bulged portion provided at the distal end part of the resin layer, the bulged portion having an outer diameter that is larger than the outer diameter of the distal end part of the resin layer.

4. The guidewire according to claim 2, further comprising:
a bulged portion provided at the distal end part of the resin layer, the bulged portion having an outer diameter that is larger than the outer diameter of the distal end part of the resin layer.

5. The guidewire according to claim 1, further comprising:
a fixation portion fixing the core shaft, the coil body, and the resin layer together at a boundary of the tapered part of the resin layer and the proximal end part of the resin layer.

6. The guidewire according to claim 2, further comprising:
a fixation portion fixing the core shaft, the coil body, and the resin layer together at a boundary of the tapered part of the resin layer and the proximal end part of the resin layer.

7. The guidewire according to claim 3, further comprising:
a fixation portion fixing the core shaft, the coil body, and the resin layer together at a boundary of the tapered part of the resin layer and the proximal end part of the resin layer.

8. The guidewire according to claim 4, further comprising:
a fixation portion fixing the core shaft, the coil body, and the resin layer together at a boundary of the tapered part of the resin layer and the proximal end part of the resin layer.

9. The guidewire according to claim 1, wherein: the coil body comprises multiple wires, and the distal end part of the resin layer enters into a space between adjacent wires of the multiple wires of the coil body.

10. The guidewire according to claim 1, wherein:
the coil body includes:
a proximal portion located at a position corresponding to the proximal end part of the resin layer in a longitudinal direction of the guidewire,
a distal portion located at a position corresponding to the distal end part of the resin layer in the longitudinal direction and having an outer diameter that is larger than an outer diameter of the proximal portion, and
an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

11. The guidewire according to claim 2, wherein:
the coil body includes:
a proximal portion located at a position corresponding to the proximal end part of the resin layer in a longitudinal direction of the guidewire,
a distal portion located at a position corresponding to the distal end part of the resin layer in the longitudinal direction and having an outer diameter that is larger than an outer diameter of the proximal portion, and
an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

12. The guidewire according to claim 3, wherein:
the coil body includes:
a proximal portion located at a position corresponding to the proximal end part of the resin layer in a longitudinal direction of the guidewire,
a distal portion located at a position corresponding to the distal end part of the resin layer in the longitudinal direction and having an outer diameter that is larger than an outer diameter of the proximal portion, and
an increasing-diameter portion located at a position corresponding to the tapered part of the resin layer in the longitudinal direction and having an outer diameter that increases in the distal direction, and the outer diameter of the distal portion of the coil body is larger than the outer diameter of the proximal end part of the resin layer.

13. The guidewire according to claim 4, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

14. The guidewire according to claim 5, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

15. The guidewire according to claim 6, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

16. The guidewire according to claim 7, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

17. The guidewire according to claim 8, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

18. The guidewire according to claim 9, wherein:
the coil body includes:
  a proximal portion located at a position corresponding to the proximal end part of the resin layer in a longitudinal direction of the guidewire,
  a distal portion located at a position corresponding to the distal end part of the resin layer in the longitudinal direction and having an outer diameter that is larger than an outer diameter of the proximal portion, and
  an increasing-diameter portion located at a position corresponding to the tapered part of the resin layer in the longitudinal direction and having an outer diameter that increases in the distal direction, and
the outer diameter of the distal portion of the coil body is larger than the outer diameter of the proximal end part of the resin layer.

19. The guidewire according to claim 1, further comprising:
  a distal end fixed part that fixes a distal end of the core shaft to the distal end of the coil body,
  wherein a distal end of the distal end part of the resin layer is spaced from the distal end fixed part in a longitudinal direction.

20. The guidewire according to claim 1, further comprising:
  a distal end fixed part that fixes a distal end of the core shaft to the distal end of the coil body,
  wherein a distal end of the distal end part of the resin layer is fixed to the distal end fixed part.

21. The guidewire according to claim 1, wherein the resin layer has an approximately constant thickness.

22. The guidewire according to claim 1, wherein the coil body has an approximately constant outer diameter.

* * * * *